United States Patent
Matsuda et al.

(10) Patent No.: US 6,177,059 B1
(45) Date of Patent: Jan. 23, 2001

(54) GPIB-LIPID COMPLEX AND USES THEREOF

(75) Inventors: Hiroshi Matsuda, Osaka; Kaeko Kamide; Yasuo Amatsuji, both of Hirakata; Takashi Imagawa, Fukuoka; Yasuo Ikeda, Tokyo; Mitsuru Murata, Niiza, all of (JP)

(73) Assignee: Yoshitomi Pharmaceutical Industries, Ltd., Osaka (JP)

(*) Notice: Under 35 U.S.C. 154(b), the term of this patent shall be extended for 0 days.

(21) Appl. No.: 09/117,746
(22) PCT Filed: Feb. 6, 1997
(86) PCT No.: PCT/JP97/00284
§ 371 Date: Dec. 3, 1998
§ 102(e) Date: Dec. 3, 1998
(87) PCT Pub. No.: WO97/29128
PCT Pub. Date: Aug. 14, 1997

(30) Foreign Application Priority Data

Feb. 7, 1996 (JP) .................................... 8-21482

(51) Int. Cl.$^7$ ................ A61K 9/127; A61K 38/17; A61K 38/36; A61K 51/08; C07K 14/705
(52) U.S. Cl. ............ 424/1.21; 424/9.321; 424/9.34; 424/9.37; 424/9.51; 424/9.6; 424/4.5; 514/7; 514/8; 514/21; 530/352; 530/359; 530/381; 530/395; 530/410
(58) Field of Search .................. 424/1.21, 9.321, 424/9.34, 9.51, 9.6, 450; 514/5, 6, 7, 8, 21; 530/352, 359, 381, 395, 410

(56) References Cited

U.S. PATENT DOCUMENTS

| | | | |
|---|---|---|---|
| 3,927,047 | * | 12/1975 | Ichikawa et al. ................... 554/63 |
| 5,399,331 | * | 3/1995 | Loughrey et al. .................. 424/450 |
| 5,428,008 | * | 6/1995 | Chao et al. ............................ 514/8 |

FOREIGN PATENT DOCUMENTS 4-506518 * 11/1992 (JP) .

OTHER PUBLICATIONS

Muszbek et al. Glycoprotein Ib and Glycoprotein IX in Human Platelets . . . J. Biol. Chem. vol. 264, No. 17, pp. 9716–9719, Jun. 15, 1989.*

Sie et al. Reconstitution of Liposomes Bearing Platelet Membrane . . . Protides Biol. Fluids, Volume Date 1981, 29th, pp. 79–83, 1982.*

* cited by examiner

Primary Examiner—Jeffrey E. Russel
(74) Attorney, Agent, or Firm—Sughrue, Mion, Zinn, Macpeak & Seas, PLLC

(57) ABSTRACT

A complex comprising a lipid and a conjugate of GPIb and lipid having a functional group, and use thereof. The GPIb-lipid complex of the present invention is extremely useful as a platelet substitute, a pharmaceutical agent for the prophylaxis and treatment of angiopathy, vascular damages and thrombosis, a diagnostic for vWF deficiency and the like, a biological or medical reagent, a reagent for screening platelet aggregation suppressant or antithrombosis, and the like. The GPIb-lipid complex of the present invention is also useful as a diagnostic for finding the location of vascular lesion or thrombus formation, or a therapeutic agent therefor, since it accumulates at vascular lesions.

27 Claims, No Drawings

GPIB-LIPID COMPLEX AND USES THEREOF

TECHNICAL FIELD

The present invention relates to a GPIb-lipid complex and use thereof. More particularly, the present invention relates to a GPIb-lipid complex that can be effectively used for the examination, diagnosis and treatment of vascular lesions and to use thereof.

BACKGROUND ART

Various glycoproteins (GP) are present on the surface of platelet membrane, and are involved in the expression of platelet functions. GPIb is one of the platelet membrane glycoproteins, and functions as a receptor of von Willebrand factor (vWF). GPIb is a heterodimer having a molecular weight of 160,000, wherein α chain and β chain form a disulfide bond.

When vascular damages are caused, platelets quickly adhere to the lesion and form platelet thrombus by aggregation and the like. In forming the platelet thrombus, vWF plays an important role as an adhesive protein. It is considered that GPIb binds with vWF as a receptor thereof and activates or promotes adhesion and aggregation of platelets via vWF at said vascular lesion. In addition, the binding of vWF and GPIb functions to stop bleeding at the vascular lesion but also forms pathologic thrombus. Thus, GPIb is expected to be effectively used for the examination and diagnosis of vascular lesion, detection of pathologic thrombus, and treatment thereof.

Nevertheless, the use of isolated GPIb has not proved successful in artificial expression of the physiological activity as mentioned above. In other words, some idea in the aspect of formulation of pharmaceutical preparations is needed to practically use GPIb as a pharmaceutical agent or reagent.

DISCLOSURE OF THE INVENTION

Under the circumstances, the present inventors have made intensive studies and first found that the physiological activity can be expressed by preparing a lipid complex comprising a conjugate of GPIb and a certain lipid and a normal lipid, which resulted in the completion of the present invention.

Accordingly, the present invention provides the following.

(1) A complex comprising a lipid and a conjugate of GPIb and a lipid having a functional group.
(2) The complex of above (1), which is in the form of a liposome.
(3) The complex of above (1), wherein the lipid is a phospholipid, glycolipid, cholesterol, fatty acid or derivative thereof.
(4) The complex of above (1), wherein the molar ratio of the GPIb:lipid is 1:10–1:1000.
(5) The complex of above (1), wherein the complex can aggregate in the presence of ristocetin.
(6) A pharmaceutical composition comprising a complex comprising a lipid and a conjugate of GPIb and a lipid having a functional group.
(7) The pharmaceutical composition of above (6), wherein the composition is a platelet substitute.
(8) The pharmaceutical composition of above (6), wherein the composition is an agent for the prophylaxis and treatment of vascular disorders, vascular damages or thrombosis.
(9) A pharmaceutical agent for examination or diagnosis, which comprises, as an active ingredient, a labeling substance and a complex comprising a lipid and a conjugate of GPIb and a lipid having a functional group.
(10) The pharmaceutical agent of above (9), wherein the labeling substance is a radioisotope, paramagnetic metal for MRI, iodide compound for X ray imaging, fluorescent substance or pigment.
(11) A drug-containing composition comprising, as an active ingredient, a drug and a complex comprising a lipid and a conjugate of GPIb and a lipid having a functional group.
(12) The composition of above (11), wherein the drug is a hemostatic agent, vasoconstrictor, antiinflammatory agent, fibrinolytic agent, anti-blood coagulator or antiplatelet agent.
(13) A conjugate of GPIb and a lipid having a functional group.
(14) The conjugate of above (13), wherein the GPIb is a GPIb itself, GPIb α chain or GPIb α chain fragment.
(15) The conjugate of above (13), wherein the GPIb is an analog, mutant, modified compound, derivative or sugar chain adduct, having a von Willebrand factor-binding capability that is almost at the same level as GPIb.
(16) The conjugate of above (13), wherein the GPIb is defective in a transmembrane site.
(17) The conjugate of above (13), wherein the lipid having a functional group is a phospholipid, glycolipid, fatty acid, glyceride, cholesterol or amphipathic lipid.
(18) The conjugate of above (13), wherein the functional group is an amino, carboxyl, thiol or aldehyde.
(19) The conjugate of above (13), wherein the GPIb and the lipid having a functional group are chemically bonded by a crosslinking agent.
(20) The conjugate of above (13), wherein the molar ratio of the GPIb:lipid having a functional group is 1:1–1:20.
(21) The complex of above (1), wherein the complex of a lipid and a conjugate of GPIb and a lipid having a functional group is prepared after preparing said conjugate.

The present invention is described in more detail in the following. (I) Conjugate of GPIb and lipid having functional group (GPIb conjugate)

① GPIb

The GPIb to be used in the present invention may be GPIb itself, its α chain, vWF binding region, namely, a GPIb fragment such as GPIb α chain [His(1)-Thr(302)] fragment and the like. An analog, a modified compound, a mutant, a derivative and a sugar chain adduct thereof are encompassed in the scope of the present invention, as long as they have almost the same level of vWF binding capability as GPIb. Moreover, they may lack a transmembrane site. In the present invention, those without this transmembrane site are preferably used.

Specific examples thereof include GPIb-related substances disclosed in WO92/ 16225, WO93/ 13784, WO93/ 16712, Japanese Patent Unexamined Publication No. 100196/ 1989, Japanese Patent Unexamined Publication No. 221394/1989 and Japanese Patent Application under PCT laid-open under kohyo No. 503708/1993.

Examples thereof include GPIb, GPIb α chain, GPIb α chain fragment, His(1)-Ala(302), His(1)-Arg(293), Ala (165)-Leu(184), Gln(180)-Phe(199), His(195)-Leu(214), Asn(210)-Val(229), Glu(225)-Ala(244), Thr(240)-Tyr(259), Asn(61)-Thr(75), Gln(71)-Ser(85), Thr(81)-Leu(95), Gln (97)-Arg(111), Leu(136)-Leu(150), Asn(210)-Ala(224), Gln (221)-Asp(235) and Ser(241)-Asp(255).

A substituted compound is exemplified by GPIb α chain fragments consisting of His(1)-Ala(302), wherein Gly(233) and Met(239) are respectively substituted by Val.

The GPIb can be prepared by any method and a method comprising extraction and isolation from platelet membrane, a method using cell culture and a production method using genetic engineering are exemplified.

②  Lipid having functional group

With regard to the lipids having a functional group, a functional group capable of directly or indirectly forming a bond with GPIb is exemplified by amino group ($NH_2$), carboxyl group (COOH), thiol group (SH), aldehyde group (CHO) and the like. As long as the functional group can form a direct or indirect bond with a GPIb molecule, it is not limited to those exemplified.

The kind of lipid is free of limitation as long as the lipid is amphipathic, such as phospholipid, glycolipid, fatty acid, glyceride, cholesterol and the like.

The lipid having a functional group is exemplified by phosphatidyl ethanolamine (hereinafter to be referred to as PE) and phosphatidyl thioethanol (e.g., 1,2-dioleoyl-sn-glycero-3-phosphatidylthioethanol) for phospholipid. When it is to be indirectly bound with GPIb, a crosslinking agent (i.e., spacer or linker) may be bonded in advance. Examples of such crosslinking agent include dicarboxylic acid, aminocarboxylic acid, bismaleimide compound, bishalocarbonyl compound, halocarbonylmaleimide compound, dithiomaleimide, dithiocarboxylic acid and maleimidecarboxylic acid. These preferably have 2 to 10 carbon atoms.

The phospholipid bonded with said crosslinking agent is exemplified by PE-N-carbonyl amine (e.g., PE-N-caproyl amine, PE-Ndodecanyl amine, PE-N-glutalyl amine and the like), PE-N-carbonyl (e.g., PE-N-succinyl, PE-N-glutalyl (NGPE), PE-N-dodecanyl (NDPE) and the like), PE-N-dithioacylate (e.g., PE-N-3-(2-pyridyldithio)propionate), PE-Nmaleimide acylate (e.g., PE-N-4-(p-maleimide phenyl) butylate and the like) and PE-N-biotinyl.

The fatty acid is exemplified by saturated or unsaturated fatty acid having 12 to 18 carbon atoms, which may be, for example, palmitic acid, oleic acid or lauric acid.

These lipids may be in the form of an acid halide, acid anhydride or active ester, for an enhanced reactivity.

③ Preparation of GPIb conjugate

GPIb and a lipid having a functional group can be directly bonded or indirectly bonded chemically via a divalent crosslinking agent. In the present invention, an indirect bond is preferred.

The molar mixing ratio of GPIb and a lipid having a functional group is about 1:1–1:20 (GPIb:lipid), preferably about 1:1–1:10.

In the chemical bond between GPIb and a lipid having a functional group, a known condensing agent or an activator of the functional group may be used as necessary. Examples of the condensing agent and the activator include carbodiimides (e.g., N,N'-dicyclohexylcarbodiimide, 1ethyl-3-(3-dimethylaminopropyl)carbodiimide (EDCI) and the like), succinimides (e.g., N-hydroxysuccinimide, N-hydroxysulfosuccinimide (NHSS) and the like), and a compound used for exchange reaction of thiol group (e.g., 5,5'-dithiobis(2-nitrobenzoic acid), 2,2'-dithiobispyridine and the like).

The divalent crosslinking agent may be a crosslinking agent having the same or different reactivity. Examples of the crosslinking agent having the same reactivity include dimethyladipinimidate, disuccinimidylsuberate and the like, and examples of the crosslinking agent having different reactivity include succinimidyl-3-(2pyridyldithio) propionate, N-(6-maleimidecaproyloxy)succinimide, Nsuccinimidyl-6-maleimide hexanoate and the like.

GPIb and a lipid having a functional group are directly bonded by a method wherein amino of PE and carboxyl group of GPIb are bonded via arbodiimide, a method wherein sugar chain of GPIb is oxidized to give aldehyde group which is bonded to form Schiff base with amine of PE, a method wherein SH group of GPIb and phospholipid having a terminal SH group (e.g., 1,2-dioleoyl-sn-glycero-3-phosphatidylthioethanol and the like) form a disulfide bond under oxidation conditions, a method wherein glycolipid is oxidized to give aldehyde group which is bonded to amino of GPIb, a method wherein fatty acid is bonded to amino of GPIb or other method.

GPIb and a lipid having a functional group are indirectly bonded by a known method such as a method wherein amino of PE and one of the carboxyl groups of crosslinking agent (dicarboxylic acid) are bonded to form amide and the other carboxyl group and amino of GPIb are bonded to form amide, a method wherein amino of PE and carboxyl group of crosslinking agent (aminocarboxylic acid) are bonded to form amide and amino of said crosslinking agent and carboxyl group of GPIb are bonded to form amide, a method wherein amino of PE and carboxyl group of crosslinking agent (aminocarboxylic acid) are bonded to form amide and amino of said crosslinking agent and aldehyde group produced by oxidation of sugar chain of GPIb are bonded to form Schiff base, a method wherein amino of PE and carboxyl group of crosslinking agent (dithiocarbonyl compound) are bonded to form amide and dithio moiety of crosslinking agent and thiol group of GPIb are reacted to form disulfide bond, a method wherein amino of PE and crosslinking agent (dithiomaleimide compound) are bonded and thiol group of GPIb is reacted to form disulfide bond, a method wherein thiol group of phosphatidylthioethanol and thiol group of GPIb are bonded by reductive alkylation using crosslinking agent (bismaleimide compound, bishalocarbonyl compound and halocarbonylmaleimide compound), and a method wherein amino of PE and carboxyl group of crosslinking agent (maleimidecarboxylic acid) are bonded to form amide and maleimide moiety of crosslinking agent and amino of GPIb are reacted.

The GPIb conjugate may be prepared in the presence of a surfactant. The surfactant is not particularly limited as long as it solubilizes the lipid having a functional group. The use of a nonionic surfactant is preferable so that the structure of GPIb will not be influenced.

In particular, a nonionic surfactant having a high critical micelle concentration (CMC), such as a CMC of not less than 1 mM, is preferable. Examples thereof include octylglucoside (n-octyl-β-D-glucoside), octylthioglucoside, (n-octyl-β-D-thioglucoside)-3-[(3-colamidepropyl) dimethylammonio]propanesulfate (CHAPS) and N,N-bis(3-D-gluconeamidepropyl)deoxycolamide (deoxy-BIGCHAP).

The mixing ratio of lipid:surfactant is preferably about 0.01:1–0.1:1 by mole.

(II) Complex of GPIb conjugate and lipid (GPIb-lipid complex)

The complex of the above-mentioned conjugate and lipid can take a form known as a lipid complex. For example, it may be a liposome, micell or a lipid emulsion, with particular preference given to liposome.

③ lipid

The lipid to be used here is free of limitation as long as it can take the form of a lipid complex such as a liposome, and may be used alone or in combination with other lipid. Examples of such lipid include phospholipid, glycolipid, cholesterol, fatty acid and derivatives thereof.

The lipid used to form said complex may be any as long as it is physiologically acceptable and can be metabolized.

Examples of the phospholipid include phosphatidylcholine (PC), phosphatidylserine, phosphatidic acid, phosphatidylglycerol, phosphatidylinositol, sphingomyelin, dicetyl phosphate, cardiolipin, lysophosphatidylcholine and the like. These lipids may be extracted and purified from a natural material such as soybean oil or egg yolk, or prepared by hydrogenation thereof to saturate the constituent fatty acid (hydrogenated phospholipid), or obtained by substituting the constituent fatty acid with specific fatty acid, such as palmitic acid and myrystin acid (e.g., diacylphosphatidylcholine, diacylphosphatidyl glycerol and the like). Specific examples thereof include purified egg yolk lecitin, hydrogenated purified soybean lecitin, egg yolk-originated phosphatidylcholine, dipalmitoylphosphatidylcholine, dipalmitoylphosphatidyl glycerol, distearylphosphatidylcholine and dimyristylphosphatidylcholine.

Glycolipid may be, for example, ceramide, cerebroside, sphingosin, sulfatide, ganglioside or glyceroglycolipids.

The fatty acid is exemplified by oleic acid, lauric acid, myristylic acid, palmitic acid and stearic acid.

Examples of lipid derivative include polyoxyethylene derivative having phosphatidyl ethanolamine and fatty acid, and polysaccharide derivative having fatty acid and cholesterol. Specifically, it may be distearyl-N-(monomethoxypolyethylene glycol succinyl)phosphatidyl ethanolamine, polyoxyethylene palmitate, N-[2-(stearoylcarboxyamino)ethyl]carbamoyl methyl mannan and N-[2-(cholesterylcarboxyamino)ethyl] carbamoylmethylpluran.

② forming a complex

The molar mixing ratio of GPIb:lipid is about 1:10–1:1000, preferably 1:50–1:200.

The lipid complex (e.g., liposome) can be prepared by, for example, surfactant removal method, hydrate method, ultrasonication, reversed phase evaporation method, freeze-thaw method, ethanol injection method, extrusion method or high pressure emulsification.

The surfactant removal method is generally gel filtration, dialysis or ultrafiltration.

The GPIb conjugate and a lipid are made into a complex after the linkage of GPIb and lipid having a functional group. That is, after preparing a GPIb conjugate, a lipid complex is formed. Alternatively, a lipid complex (liposome) consisting of the lipid having a functional group of (I)② and the lipid of (II)① may be prepared first and GPIb is then added to bond the lipid having a functional group and GPIb, whereby a GPIb-lipid complex can be prepared.

The GPIb-lipid complex can be isolated and purified by a known method such as centrifugation and gel filtration.

The production method of the GPIb-lipid complex is exemplified in the following.

(i) Preparation of GPIb-lipid complex after making GPIb conjugate

GPIb, lipid [(II)①] and lipid [(II)②] having a functional group solubilized with surfactant are mixed in a suitable aqueous solvent to allow formation of a bond of GPIb and the lipid having a functional group. Then the surfactant is removed to give a GPIb-lipid complex.

Alternatively, GPIb and a lipid having a functional group may be mixed in the presence of a surfactant to give GPIb conjugate, and then a lipid may be added and the surfactant may be removed.

The unreacted GPIb, lipid and the like may be separated and removed to give a purified product.

The surfactant is the same as above. The mixing ratio (lipid:surfactant) is about 0.001–0.1:1 (molar ratio).

(ii) Preparation of GPIb-lipid complex by bonding GPIb after forming lipid complex (liposome)

The lipid [(I)②] having a functional group and lipid [(II)①] are dissolved and mixed in an organic solvent such as chloroform and ethanol, and the organic solvent is removed to give a thin lipid membrane. A suitable aqueous solvent is added and the mixture is treated by a known method, such as shaking and stirring, to give a lipid complex. GPIb is added to form a bond of GPIb and the lipid having a functional group, whereby a GPIb-lipid complex is formed.

The unreacted GPIb, lipid and the like may be separated and removed to give a purified product.

The proportion of GPIb in the obtained GPIb-lipid complex is 0.01–10 parts by weight, preferably 0.1–5 parts by weight, per part by weight of the lipid.

The obtained GPIb-lipid complex has a particle size of about 50–500 nm, preferably about 100–400 nm. The number of GPIb molecules per particle is 250–3000 and surface density of GPIb is $10^{11}$–$10^{12}$.

The GPIb-lipid complex (e.g., liposome) has a structure of multilamella vesicle (MLV), small unilamella vesicle, large unilamella vesicle and the like. It may be coated with a hydrophillic polymer such as polyethylene glycol (PEG), Pluronic(™) (copolymer of polyoxyethylene and polyoxypropylene and the like.

Where necessary, the obtained GPIb-lipid complex is washed with a physiologically acceptable aqueous solution, sterilized by filtration and dispensed and formulated into a liquid, pellet or suspension preparation.

The complex can be processed by a method known to be usable for the preparation of pharmaceutical products. The above-mentioned preparations may be provided as lyophilized preparations upon freezing a liquid preparation and drying same under reduced pressure.

For lyophilization, a monosaccharide (e.g., glucose), disaccharides (e.g., sucrose) and the like may be added.

The above-mentioned preparations may contain, as a stabilizer, at least one polymer selected from albumin, dextran, vinyl polymer, gelatin and hydroxylethyl starch.

The polymer may be incorporated into the gaps present in said lipid complex together with a drug. Alternatively, the polymer may be added to or contained in said lipid complex preparation containing a drug. This means that the polymer may be added or contained outside the liposome. It is needless to say that it can be incorporated inside or outside the lipid complex.

The stabilizer is added in an amount of 0.5–10 parts by weight, preferably 1–5 parts by weight, per part by weight of the lipid.

(III) Use of GPIb-lipid complex as pharmaceutical agent

The GPIb-lipid complex of the present invention can be embodied as a diagnostic of von Willebrand deficiency and the like by adding a labeling substance (so-called marker).

Examples of such labeling substance include RI (radioisotope), paramagnetic metal for MRI, iodide compound for X ray imaging and fluorescent substance.

RI is exemplified by $^{3}H$, $^{14}C$, $^{99m}Tc$, $^{123}I$, $^{131}I$, $^{87m}Sr$, $^{113m}In$ and $^{197}Hg$. The paramagnetic metal for MRI is exemplified by divalent ion and trivalent ion of a paramagnetic metal of chromium (Cr), gadrinium (Gd), manganese (Mn), iron (Fe), cobalt (Co), nickel (Ni), praseodymium (Pr), neodium (Nd), samarium (Sm), ytterbium (Yb), terbium (Tb), dysprosium (Dy), hormium (Ho), erbium (Er), copper (Cu) and the like, with preference given to divalent ion and trivalent ion of gadrinium (Gd), terbium (Tb), dysprosium (Dy), hormium (Ho), erbium (Er) and iron (Fe).

The iodide compound for X ray imaging may be a known compound for X ray imaging. Examples thereof include adipiodone, amidotrizoic acid, iothalamic acid, iopanoic acid, iobenzamic acid, iopodate, tyropanoic acid, iopydol, iopydone, propyliodone, iodamide and salts thereof (e.g., sodium salt and meglumine salt).

The fluorescent substance may be, for example, fluorescein isothiocyanate (FITC), carboxyfluorescein (CF) and the like. These labeling substances can be encapsulated in a lipid complex (liposome) by a known method. For example, it can be enclosed in a lipid complex in the form of a salt or after chelating with a chelating agent such as ethylenediaminetetraacetic acid (EDTA) and diethylenetriamino pentaacetic acid (DTPA).

In the case of $^{99m}$Tc, for example, sodium pertechnetate, technetium polyphosphate or $^{99m}$Tc DTPA can be used.

The GPIb-lipid complex of the present invention is cumulative at the vascular lesion and thus, may be formed into a composition containing a drug (drug vehicle).

The drug to be contained is free of particular limitation as long as it proves physiologically and pharmacologically effective upon accumulation thereof at the vascular lesion, and may be, for example, a hemostatic agent, vasoconstrictor, antiinflammatory agent, fibrinolytic agent, anti-blood coagulator or anti-platelet agent.

The hemostatic agent is exemplified by carbazochrome, blood coagulation factor (FVIII, FIX), thrombin, antiplasmin agent (e.g., ε-aminocaproic acid and tranexamic acid), protamine sulfate, etamsylate, phytonadione and conjugated estrogen (e.g., sodium estrone sulfate and sodium equilin sulfate) and the like.

The vasoconstrictor is exemplified by noradrenaline, norfenefrine, phenylephrine, metaraminol, methoxamine, prostaglandin $F_1 \alpha$, prostaglandin $F_2 \alpha$, thromboxane $A_2$ and the like.

The antiinflammatory agent is exemplified by steroidal antiinflammatory agent (e.g., dexamethasone, hydrocortisone, prednisolone, betamethasone, triamcinolone and methylprednisolone and the like), non-steroidal antiinflammatory agent (e.g., indometacin, acemetacin, flurbiprofen, aspirin, ibuprofen, flufenamic acid, and ketoprofen) and the like.

The fibrinolytic agent is exemplified by plasmin, tissue plasminogen activator, urokinase, precursor thereof and derivatives thereof.

The anti-blood coagulator is exemplified by acidic mucopolysaccharide (e.g., heparin), coumarin anti-blood coagulator, natural extract (e.g., hirudine) and derivatives thereof, physiologically active substances (e.g., thrombomodulin and active protein C) and the like.

The anti-platelet agent is exemplified by aspirin, ticlopidine, cilostazol, prostacyclin and the like.

These drugs can be encapsulated in a lipid complex by a known method.

The inventive GPIb-lipid complex is administered in an amount of about 0.001–1000 mg as GPIb per day. The dose can be appropriately varied depending on the sex, age and symptoms of patients.

The GPIb-lipid complex is more preferably administered parenterally. To be specific, it is administered by intravascular (intraarterial or intravenous) injection, intravenous drip, subcutaneous administration, local administration, intramuscular administration and the like.

The pharmaceutical composition containing the inventive GPIb-lipid complex is useful as a platelet substitute, a pharmaceutical product for the prophylaxis and treatment of angiopathy, vascular damages and thrombosis, a diagnostic for vWF deficiency and the like, a biological or medical reagent, a reagent for screening platelet aggregation suppressant or antithrombosis, and the like. It is also useful for a diagnostic for finding the location of vascular lesion or thrombus formation, or a therapeutic agent therefor.

The present invention is explained in more detail in the following by way of examples and experimental examples, to which the present invention is not limited.

EXAMPLE 1

(1) Preparation of activated NGPE

To NGPE (500 μg) was added 1 w/v% octylglucoside/ 0.02M 2-(N-morpholino)ethanesulfonate (MES) buffer (500 μl, pH 5.0, containing 0.15 M NaCl). Thereto were added 0.25 M EDCI/same MES buffer (125 μ and 0.1 M NHSS/ same MES buffer (125 μl), and the mixture was incubated at room temperature for 10 min. Using Amicon 30 (fraction molecular weight 30,000), the incubate was subjected to ultrafiltration using 0.5 w/v% octylglucoside/0.05 M 2-[4-(2-hydroxyethyl)-1-piperadinyl]ethanesulfonate (HEPES) buffer (containing 0.11 M NaCl, pH 8.0).

(2) Preparation of GPIb liposome

GPIb α chain fragment [His(1)-Arg(293), molecular weight 45,000], 3 mg, genetically produced using CHO cells, was dissolved in 0.05M HEPES buffer (containing 0.11 M NaCl, pH 8.0) and PC solution prepared by dissolving egg yolk phosphatidylcholine (EPC, 46.4 mg), cholesterol (11.6 mg), dipalmitoylphosphatidyl glycerol (DPPG, 9.6 mg) and octylglucoside (250.6 mg) in said HEPES buffer (680 μl) was added. Further, activated NGPE prepared in Example 1(1) was added.

The mixing ratio (molar ratio) of EPC:cholesterol:DPPG:GPIb was adjusted to be 100:50:20: 1, that of EPC:octylglucoside was adjusted to be 0.07:1, and that of activated NGPE:GPIb was adjusted to be 10:1.

Incubation at 37° C. for 4 hr gave liposome. By gel filtration (carrier: Sephadex G-75), octylglucoside was removed.

The GPIb liposome was recovered by ultracentrifugation by CsCl density gradient under the following conditions. That is, CsCl 1500 mg was dissolved in 1 ml of a sample and 40% CsCl (1 ml) and physiological saline (0.2 ml) were layered, which was followed by centrifugation at 55,000 rpm for 30 min.

The prepared GPIb liposome had a PC concentration of 1.365 mg/ml, protein concentration of 0.978 mg/ml and average particle size of 328 nm.

EXAMPLE 2

CF was added to phospholipid in a proportion of 0.1 part by weight per part by weight of phospholipid. The mixture was formulated in the same manner as in Example 1 to give a GPIb-lipid complex containing CF.

EXAMPLE 3

Blood coagulation factor FVIII was added to phospholipid in a proportion of 0.1 part by weight per part by weight of phospholipid. The mixture was formulated in the same manner as in Example 1 to give a GPIb-lipid complex containing FVIII.

EXAMPLE 4

Prostaglandin $F_1\alpha$ was added to phospholipid in a proportion of 0.01 part by weight per part by weight of phospholipid. The mixture was formulated in the same manner as in Example 1 to give a GPIb-lipid complex containing Prostaglandin $F_1\alpha$.

EXAMPLE 5

In the same manner as in the drug formulation in Example 1 except the use of NDPE instead of NGPE, GPIb liposome was prepared.

COMPARATIVE EXAMPLE 1

In the same manner as in Example 1 except the binding of GPIb, liposome was obtained.

EXPERIMENTAL EXAMPLE 1

Aggregation capability of GPIb liposome was confirmed. The GPIb liposome ($2 \times 10^{12}$ liposomes/ml) prepared in Example 1 was reacted in the presence of vWF (50 μg/ml) and ristocetin (1 mg/ml) for 10 min and clot was measured with light scattering agglutination meter.

Using the same system, effect on liposome aggregation capability by the addition of vWF antibody (μg/ml) or GPIb antibody (50 μg/ml) was examined. In addition, the effect in the absence of ristocetin was also confirmed.

Also, the liposome ($2 \times 10^{12}$ liposomes/ml) without GPIb binding as prepared in Comparative Example 1 was reacted in the presence of vWF (50 μg/ml) and ristocetin (1 mg/ml) for 10 min and clot was measured with light scattering agglutination meter.

The results are shown in the following Table.

|  | vWF | ristocetin | Other additives | Clot |
|---|---|---|---|---|
| GPIb liposome |  |  |  |  |
| $2 \times 10^{12}$ liposomes/ml | 50 μg/ml | 1 mg/ml | none | formed |
| $2 \times 10^{12}$ liposomes/ml | 50 μg/ml | 1 mg/ml | vWF antibody 50 μg/ml | Not formed |
| $2 \times 10^{12}$ liposomes/ml | 50 μg/ml | 1 mg/ml | GPIb antibody 50 μg/ml | Not formed |
| $2 \times 10^{12}$ liposomes/ml | 50 μg/ml | none | none | Not formed |
| Liposome without GPIb |  |  |  |  |
| $2 \times 10^{12}$ liposomes/ml | 50 μg/ml | 1 mg/ml | none | Not formed |

EXPERIMENTAL EXAMPLE 2

Various GPIb-lipid complexes prepared in Examples 2–5 were treated in the same manner as in Experimental Example 1 to confirm aggregation capability. As a result, every preparation specifically reacted with vWF in the presence of ristocetin and formed a clot.

The GPIb liposome specifically reacted with vWF in the presence of ristocetin and formed a clot. This clot formation was completely inhibited by the addition of vWF antibody or GPIb antibody. In the absence of ristocetin, aggregation did not occur. On the other hand, a liposome without GPIb did not form a clot in the presence of ristocetin.

Thus, GPIb liposome can bind with vWF and form a clot. This proves that the GPIb liposome is useful as a platelet substitute.

EXPERIMENTAL EXAMPLE 3

Aggregation of GPIb liposome and vWF

GPIb liposome labeled with pigment (rhodamine) and vWF labeled with FITC were used to produce ristocetin aggregation according to the method of Experimental Example 1. As a result, aggregation of GPIb liposome and vWF was similarly observed both by rhodamine detection and FITC detection.

EXPERIMENTAL EXAMPLE 4

GPIb liposome taken-in by platelet clot

A mixed solution of normal platelet and rhodamine-labeled GPIb liposome was treated in the same manner as in Experimental Example 1 to cause ristocetin aggregation. As a result, GPIb liposome was taken into platelet clot as microscopically observed by detecting rhodamine.

EXPERIMENTAL EXAMPLE 5

Promotion of aggregation of platelets reduced in number due to addition of GPIb liposome GPIb liposome was added under the conditions where clots are less formed due to the reduced number of platelets, so that the concentration became 15, 60 and 240 μg/ml, and the mixtures were treated in the same manner as in Experimental Example 1 to cause ristocetin aggregation. The formation of clots was confirmed with an aggregation meter. As a result, dose-dependently greater clots were found, which proves promotion of aggregation.

FIELD OF INDUSTRIAL APPLICABILITY

The GPIb-lipid complex of the present invention can bind with vWF and form an aggregate. Thus, it is expected to have a potential of being practically used in a wide range as a platelet substitute, a pharmaceutical agent for the prophylaxis and treatment of angiopathy, vascular damages and thrombosis, a diagnostic for vWF deficiency and the like, a biological or medical reagent, a reagent for screening platelet aggregation suppressant or antithrombosis, and the like. The GPIb-lipid complex of the present invention is also useful as a diagnostic for finding the location of vascular lesion or thrombus formation, or a therapeutic agent therefor, since it specifically accumulates at vascular lesions.

This application is based on application No. 21482/1996 filed in Japan, the content of which is incorporated hereinto by reference.

What is claimed is:

1. A complex comprising a lipid and a conjugate of GPIb or a GPIB fragment having a von Willebrand factor-binding capability that is almost at the same level as GPIb itself and a lipid having a functional group, with the proviso that the GPIb fragment is defective in a transmembrane site and the lipid having a functional group is not a fatty acid.

2. The complex of claim 1, which is in the form of a liposome.

3. The complex of claim 1, wherein the lipid is a phospholipid, glycolipid or cholesterol.

4. The complex of claim 1, wherein the molar ratio of the GPIb fragment:lipid is 1:10–1:1000.

5. The complex of claim 1, wherein the complex can aggregate in the presence of ristocetin.

6. A pharmaceutical composition comprising a complex comprising a lipid and a conjugate of GPIb fragment having a von Willebrand factor-binding capability that is almost at the same level as GPIb itself and a lipid having a functional group, with the proviso that the GPIb fragment is defective in a transmembrane site and the lipid having a functional group is not a fatty acid.

7. The pharmaceutical composition of claim 6, wherein the composition is a platelet substitute.

8. The pharmaceutical composition of claim 6, wherein the composition is an agent for the prophylaxis or treatment of vascular disorders, vascular damages or thrombosis.

9. A pharmaceutical agent for examination or diagnosis, which comprises, as an active ingredient, a labeling substance and a complex comprising a lipid and a conjugate of GPIb fragment having a von Willebrand factor-binding capability that is almost at the same level as GPIb itself and a lipid having a functional group, with the proviso that the GPIb fragment is defective in a transmembrane site and the lipid having a functional is not a fatty acid.

10. The pharmaceutical agent of claim 9, wherein the labeling substance is a radioisotope, paramagnetic metal for MRI, iodide compound for X ray imaging, fluorescent substance or pigment.

11. A drug-containing composition comprising, as an active ingredient, a drug and a complex comprising a lipid and a conjugate of GPIb fragment having a von Willebrand factor-binding capability that is almost at the same level as GPIb itself and a lipid having a functional group, with the proviso that the GPIb fragment is defective in a transmembrane site and the lipid having a functional group is not a fatty acid.

12. The composition of claim 11, wherein the drug is a hemostatic agent, vasoconstrictor, antiinflammatory agent, fibrinolytic agent, anti-blood coagulator or anti-platelet agent.

13. A conjugate of GPIb or fragment having a von Willebrand factor-binding capability that is almost at the same level as GPIb itself and a lipid having a functional groups with the proviso that the GPIb fragment is defective in a transmembrane site and the lipid having a functional group is not a fatty acid.

14. The conjugate of claim 13, wherein the GPIb fragment is a GPIb α chain or GPIbα chain fragment.

15. The conjugate of claim 13, wherein the GPIb fragment is a substituted compound or sugar chain adduct.

16. The conjugate of claim 13, wherein the lipid having a functional group is a phospholipid, glycolipid, glyceride, cholesterol or amphipathic lipid.

17. The conjugate of claim 13, wherein the functional group is an amino, carboxyl, thiol or aldehyde.

18. The conjugate of claim 13, wherein the GPIb fragment and the lipid having a functional group are chemically bonded by a crosslinking agent.

19. The conjugate of claim 13, wherein the molar ratio of the GPIb fragment:lipid having a functional group is 1:1–1:20.

20. The complex of claim 1, wherein the complex of a lipid and a conjugate of GPIb fragment and a lipid having a functional group is prepared after preparing said conjugate.

21. The complex of claim 1, wherein the lipid having a functional group is a phospholipid.

22. The pharmaceutical composition of claim 6, wherein the lipid having a functional group is a phospholipid.

23. The pharmaceutical agent of claim 9, wherein the lipid having a functional group is a phospholipid.

24. The drug-containing composition of claim 11, wherein the lipid having a functional group is a phospholipid.

25. The conjugate of claim 13, wherein the lipid having a functional group is a phospholipid.

26. The conjugate of claim 13, wherein the lipid having a functional group is a phosphatidyl ethanolamine (PE), phosphatidyl thioethanol, PE-N-carbonyl amine, PEN-carbonyl, PE-N-dithioacylate, PE-N-maleimide acylate or PE-N-biotinyl.

27. The conjugate of claim 14, wherein the GPIb α chain fragment is His(1)-Ala(302), His(1)-Arg(293), His(1)-Ala (302) wherein Gly(233) is substituted by Val or His(1)-Ala (302) wherein Met(239) is substituted by Val.

* * * * *

UNITED STATES PATENT AND TRADEMARK OFFICE
CERTIFICATE OF CORRECTION

PATENT NO.     : 6,177,059 B1
DATED          : January 23, 2001
INVENTOR(S)    : Hiroshi Matsuda, Kaeko Kamide, Yasuo Amatsuji, Takashi Imagawa, Yasuo Ikeda, and Mitsuru Murata It is certified that error appears in the above-identified patent and that said Letters Patent is hereby corrected as shown below:

<u>Column 10,</u>
Line 39, delete "or a GPIB".

<u>Column 11,</u>
Line 21, delete "or".

Signed and Sealed this

Fourteenth Day of May, 2002

*Attest:*

*Attesting Officer*

JAMES E. ROGAN
*Director of the United States Patent and Trademark Office*